United States Patent
Har-Noy (10) Patent No.: US 11,833,173 B2
(45) Date of Patent: *Dec. 5, 2023

(54) TH1 VACCINATION PRIMING FOR ACTIVE IMMUNOTHERAPY

(71) Applicant: Mirror Biologics, Inc., Mesa, AZ (US)

(72) Inventor: Michael Har-Noy, Jerusalem (IL)

(73) Assignee: Mirror Biologics, Inc., Wesley Chapel, FL (US)

( * ) Notice: Subject to any disclaimer, the term of this patent is extended or adjusted under 35 U.S.C. 154(b) by 551 days.

This patent is subject to a terminal disclaimer.

(21) Appl. No.: 16/928,884

(22) Filed: Jul. 14, 2020

(65) Prior Publication Data

US 2020/0338127 A1    Oct. 29, 2020

Related U.S. Application Data

(60) Division of application No. 15/630,592, filed on Jun. 22, 2017, now Pat. No. 10,744,158, which is a continuation of application No. 12/570,442, filed on Sep. 30, 2009, now Pat. No. 9,695,397.

(60) Provisional application No. 61/101,692, filed on Oct. 1, 2008.

(51) Int. Cl.
| | |
|---|---|
| A61K 35/17 | (2015.01) |
| A61K 39/00 | (2006.01) |
| C12N 5/0783 | (2010.01) |
| A61K 35/02 | (2015.01) |
| A61K 35/12 | (2015.01) |

(52) U.S. Cl.
CPC .......... *A61K 35/17* (2013.01); *A61K 39/0011* (2013.01); *C12N 5/0636* (2013.01); *A61K 2035/124* (2013.01); *A61K 2039/5152* (2013.01); *A61K 2039/5158* (2013.01); *A61K 2039/545* (2013.01); *A61K 2039/57* (2013.01); *C12N 2501/23* (2013.01); *C12N 2501/51* (2013.01); *C12N 2501/515* (2013.01)

(58) Field of Classification Search
None
See application file for complete search history.

(56) References Cited

U.S. PATENT DOCUMENTS

| | | |
|---|---|---|
| 7,402,431 B2 | 7/2008 | Har-Noy |
| 7,435,592 B2 | 10/2008 | Har-Noy |
| 2002/0131960 A1 | 9/2002 | Sadelain et al. |
| 2002/0160502 A1 | 10/2002 | Chung et al. |
| 2003/0134415 A1 | 7/2003 | Gruenberg |

(Continued)

FOREIGN PATENT DOCUMENTS

WO    2003034820    5/2008

OTHER PUBLICATIONS

PCT International Search Report, dated May 25, 2010.
(Continued)

*Primary Examiner* — Amy E Juedes
(74) *Attorney, Agent, or Firm* — Westman, Champlin & Koehler, P.A.; Z. Peter Sawicki (57) ABSTRACT

The present invention includes vaccine compositions and methods for using these vaccine compositions in active immunotherapy. The vaccine compositions include allogeneic activated Th1 memory cells. The compositions can also include one or more disease-related antigens. The methods include administering the vaccine compositions to provide a Th1 footprint in normal individuals or patients susceptible to disease or having minimal residual disease.

8 Claims, 9 Drawing Sheets

(56) References Cited

U.S. PATENT DOCUMENTS

| | | |
|---|---|---|
| 2003/0202985 A1 | 10/2003 | Paterson |
| 2004/0013649 A1 | 1/2004 | Tam et al. |
| 2004/0115224 A1 | 6/2004 | Ohno |
| 2004/0228848 A1 | 11/2004 | Har-Noy |
| 2005/0191291 A1 | 9/2005 | Har-Noy |
| 2005/0214274 A1 | 9/2005 | Har-Noy |
| 2006/0257412 A1 | 11/2006 | Bowdish et al. |
| 2007/0025958 A1 | 2/2007 | Hadden |
| 2008/0199495 A1 | 8/2008 | Boyd |

OTHER PUBLICATIONS

PCT Written Opinion, dated May 24, 2010.
Beck, O. et al. (2006) "Generation of highly purified and functionally active human T(H)1 cells against Aspergillus fumigatus." Blood, vol. 107, No. 6, pp. 2526-2569.
Har-Noy, M. et al. (2008) "Allogeneic CD3/CD28 cross-linked Th1 memory cells provide potent adjuvant effects for active immunotherapy of leukemia/lymphoma.", Leuk Res. vol. 33, No. 4, pp. 525-538.
M. Har-Noy, et al. Completely mismatched allogeneic CD3/CD28 cross-linked Th1 memory cells elicit anti-leukemia effects in unconditioned hosts without GVHD toxicity. Leukemia Research, 2008, 32(12): 1903-1913.
Jung U. et al. (2003) "CD3/CD28-costimulated T1 and T2 subsets: differential in vivo allosensitizetion generates distinct GVT and GVHD effects." Blood, vol. 102, No. 9, pp. 3439-3446.
Shankaran et al. "IFNγ and lymphocytes prevent primary tumour development and shape tumour immunogenicity" Nature Apr. 2001; 410:1107-1111.
Smith R.A. et al. "Key Criteria in the Decision to Screen" Holland-Frei Cancer Medicine. 2003 6th edition.
Trinchieri G et al. "Immunoregulation by interleukin-12." J Leukoc Biol. Apr. 1996;59(4):505-11.
Trinchieri G et al. "Interleukin-12: a proinflammatory cytokine with immunoregulatory functions that bridge innate resistance and antigen-specific adaptive immunity" Annu. Rev. Immunol. 1995 13:251-76.
Final Rejection for Japanese Patent Application No. 2011-530213, dated Dec. 15, 2014.
Extended European Search Report; 09818495.5; Dec. 12, 2012.
Chinese Office Action; Application No. 200980147749.6; dated Aug. 20, 2013.
Office Action issued in related Japanese patent application No. 2016-38729, dated Dec. 6, 2016.
Yu et al. "Priming with CpG-enriched plasmid and boosting with protein formulated with CpG oligodeoxynucleotides and Quil A induces strong cellular and humoral immune responses to hepatitis C virus NS3", Journal of General Virology (2004) 85, 1533-1543.
Rapoport et al., 2005, Nat. Immunol. vol. 11:1230-1237.
Burgers et al., 2005, Best Pract. Res. Clin. vol. 19: 277-291.
Armstrong et al., 2001, Brit. J. Radiol. vol. 74: 991-1002.
Porter et al., 2006, Blood vol. 107: 1325-1331.
Wang et al., 1999, Nat. Med. vol. 5: 1004-1009.
Osborne et al., 1973, J Exp. Med. vol. 138: 825-838.
Theodorou et al., 2008, Clin. Exp. Immunol. vol. 152:456-63.
Chipps et al., 2006, Expert. Opin. Ther. Target, vol. 11: 1-10.
Kidd, 2003, Altern Med Rev, vol. 8: 223-246.
Eyre et al., 2000, Cancer Screening and Early Detection.
Hansen et al., 1999, J. Clin. Invest. 103: 175-183.
Graner et al. "Tumor-derived chaperone-rich cell lysates are effective therapeutic vaccines against a variety of cancers" Canc. Immunother (2003) vol. 52: 226-234.
McCarthy et al., 2003, Genome Biol. vol. 4: 119.1-119.8.

TH1 VACCINATION PRIMING FOR ACTIVE IMMUNOTHERAPY

The present application is a divisional of U.S. patent application Ser. No. 15/630,592, filed Jun. 22, 2017, which is a continuation of U.S. patent application Ser. No. 12/570,442, filed Sep. 30, 2009, which is based on and claims the benefit of U.S. provisional patent application Ser. No. 61/101,692, filed Oct. 1, 2008, the contents of which are hereby incorporated by reference in their entireties.

FIELD OF INVENTION

The present invention relates to the field of vaccines, and more particularly to therapeutic vaccine methods. Specifically, the invention relates to methods for use of pharmaceutical compositions containing allogeneic cells for priming for increased Th1 memory that can later be activated and serve as an adjuvant for active immunotherapy of cancer and infectious diseases and other diseases of aging.

BACKGROUND OF THE INVENTION

Harnessing the power of the immune system to treat chronic infectious diseases or cancer is a major goal of immunotherapy. Vaccination (a/k/a, active immunotherapy) methods are designed to activate the immune system to specifically recognize and protect against invading pathogens. For over 200 years, active immunotherapy approaches have been used to prevent numerous infectious diseases, including small pox, rabies, typhoid, cholera, plague, measles, varicella, mumps, poliomyelitis, hepatitis B and the tetanus and diphtheria toxins.

Active immunotherapy concepts are now being applied to develop therapeutic cancer vaccines with the intention of treating existing tumors or preventing tumor recurrence, as well as being applied to the treatment of chronic viral infections. However, existing active immunotherapy technology has not been successful in protecting against many of the modern disease targets such as HIV/AIDS, Hepatitis C and cancer. This is in part due to the inability of current vaccination technology to elicit the correct type of immune responses.

The type of immune response generated to infection or other antigenic challenge can generally be distinguished by the subset of T helper (Th) cells involved in the response. Immune responses can be broadly divided into two types: Th1 and Th2. Th1 immune activation is optimized for intracellular infections such as viruses and involves the activation of Natural Killer (NK) cells and Cytolytic T-cells (CTL) that can lyse infected cells, whereas Th2 immune responses are optimized for humoral (antibody) responses. Th1 immune activation is the most highly desired for cancer therapy and Th2 immune responses are directed more at the secretion of specific antibodies and are relatively less important for tumor therapy. Prior art vaccine compositions are specialized in eliciting Th2 or humoral immune responses, which is not effective against cancers and most viral diseases.

Cancer eradication and maintenance of remission requires Th1 immune activation. Therefore, one of the goals of active immunotherapy is to develop methods which are capable of deviating a resident Th2 response to a Th1 response. However, in some patients which develop a potentially effective Th1 immune response against a tumor or are therapeutically immunized to develop a Th1 immune response, the tumors still continue to grow unaffected.

This lack of efficacy in Th1 immune patients and the ineffectiveness of native immune responses against tumors has been attributed to the ability of tumors to employ various strategies for evasion from immune attack. These immunoavoidance mechanisms employed by tumors render the immune system tolerant and permit tumors to grow unimpeded by immune surveillance even after specific upregulation of anti-tumor effector mechanisms by active immunotherapy. Therefore, active immunotherapy strategies require in addition to an immunomodulatory mechanism of action, a strategy to overcome tumor immunoavoidance mechanisms.

Establishment of self-tolerance to a tumor is thought to be related to existing natural immune mechanisms which are normally employed to prevent autoimmune disease. That this normally beneficial effect may be responsible for tumor immune evasion is supported by the observation that many of the tolerance mechanisms that prevent autoimmunity are the same as employed by tumors to prevent immune destruction. The "danger hypothesis" proposes that the immune system does not primarily discriminate self from non-self, but instead is mainly adapted to recognize and respond to antigens depending on the context in which the antigens are presented to the immune system.

The use of adjuvants has long been a strategy for influencing the immune response to antigens in a vaccine composition. Aluminum salts, and squalene oil in water emulsion (MF59) are the most widely used adjuvants in human vaccines. However, these adjuvants predominately promote Th2 responses to antigens, and while effective at elevating serum antibody titers do not elicit significant cellular immune responses.

SUMMARY OF THE INVENTION

This disclosure describes compositions and methods for priming individuals with alloantigens to develop high titers of anti-allogeneic memory cells of the Th1 phenotype. Primed individuals present with an infectious disease or cancer can then undergo active immunotherapy with the same alloantigens as adjuvant. The introduction of alloantigen in a primed individual provides a strong burst of Th1 cytokines which has a powerful adjuvant effect The priming method is particularly beneficial for elderly individuals in maintaining immune health, as the number of Th1 cells tend to be lower as individuals increase in age.

The methods described herein provide a means to increase the number of Th1 cells in circulation (the "Th1 footprint") in patients by the administration of living allogeneic cells which produce Th1 cytokines. Allogeneic cells contain alloantigens which are processed by immune cells and lead to the development of anti-allogeneic immunity. When the allogeneic cells are made to produce Th1 cytokines these cytokines serve as an adjuvant to cause the immune response to the alloantigens to be steered to Th1, thus increasing the Th1 footprint of a patient. Multiple injections of the allogeneic cells producing Th1 cytokines serves to boost this Th1 footprint The priming vaccinations are generally administered to patients with high susceptibility to diseases such as elderly patients. The priming vaccinations may also be administered to patients who have had cancer but are in remission and might be harboring minimal residual disease but not a full tumor challenge. The Th1 footprint generated by the priming enables the patient's immune system to be activated to produce Th1-steering cytokines at any time in the future by injecting additional antigenic challenge. In other words, the patient's immune system is primed and in a standby mode. Thus, when a primed patient develops disease, vaccine compositions that include the allogeneic cells can be administered to patients alone or in combination with antigen from the disease. This priming of a patient to generate a Th1 footprint flowed by active immunotherapy allows the immune system to more effectively mount a therapeutic response. Patients with existing disease can also be primed prior to active immunotherapy.

In a one aspect, this disclosure includes a method of vaccinating a patient against a disease. The method includes administering a priming composition of allogeneic activated Th1 memory cells to provide a Th1 footprint in the patient wherein the priming composition is administered when the patient is not exhibiting symptoms of the disease.

In another aspect, this disclosure includes a method of reducing recurrence of a disease in a patient. The method includes administering to the patient a priming composition of allogeneic activated Th1 memory cells and disease-related antigens.

In a further aspect, this disclosure includes a method of developing a Th1 footprint in a patient to serve as an adjuvant to activate immunotherapy. The method includes administering a priming composition that includes allogeneic activated Th1 memory cells wherein the priming composition is administered when the patient is not exhibiting symptoms of the disease.

In a yet another aspect, this disclosure includes a therapeutic composition for treating a disease in a patient. The composition includes allogeneic activated Th1 memory cells wherein the therapeutic composition upon administration increases the number of Th1 cells in circulation in a patient.

In yet another aspect, this disclosure includes a use of a composition comprising allogeneic Th1 memory cells in the manufacture of a medicament for the treatment of a disease by increasing the number of Th1 cells in circulation after treatment.

In yet another aspect, this disclosure includes a vaccine composition kit for a patient against a tumor or a pathogen. The kit includes a priming composition and an activating composition, wherein the priming and the activating composition both comprise allogeneic activated Th1 memory cells from the same source and wherein the priming composition upon administration increases the number of Th1 cells in circulation in a patient.

DETAILED DESCRIPTION OF THE ILLUSTRATIVE EMBODIMENTS

The present invention includes priming vaccine compositions and methods for using these priming vaccine compositions in active immunotherapy. Preferably, the priming vaccine compositions include allogeneic Th1 memory cells that are activated at the time of injection. The methods include administering the priming vaccine compositions to provide a Th1 footprint in normal individuals or patients susceptible to disease or having minimal residual disease. The Th1 footprint in these individuals can then be mobilized by active immunotherapy at the onset or recurrence of a disease by administering an activating vaccine composition that includes allogeneic Th1 memory cells. The activating vaccine composition may also include disease-related antigens. The activating vaccine composition may be used to elicit therapeutic Th1 immunity in patients while also providing the means to overcome the immunoavoidance mechanisms of the disease pathogens and tumors. The priming of the patient advantageously creates a powerful in-situ adjuvant for steering Th1 immunity. Thus, when the patient is exposed to a pathogen or cancer challenge the immune system is able to mount a more timely and effective response.

The present invention includes a priming vaccine composition that comprises living immune cells, where at least a portion are T-cells. The T-cells are preferably memory T-cells (CD45RO+, CD62$^{Lo}$) of the Th1 phenotype (CD4+ T-cells that produce IFN-γ and not IL-4) and referred to herein as "memory cells" or "memory Th1 cells". The memory Th1 cells are activated at the time of formulation and introduction to a patient. The preferred activation method is by the cross-linking of CD3 and CD28 surface molecules on the T-cells. The activated memory T-cells preferably express CD40L upon being activated and produce large amounts of inflammatory cytokines (such as IFN-γ, GM-CSF, and TNF-α). These activated Th1 memory cells are preferably allogeneic to the patient. In some embodiments, the priming composition may also include disease related antigenic material.

The composition with activated Th1 memory cells may be used for prophylactic purposes or therapeutic purposes, or both. The priming compositions described herein are particularly preferable when administered to individuals who have not exhibited any symptoms of a disease. Even more preferable is administering the priming compositions to patients who have not exhibited any symptoms but are susceptible to a disease. The priming composition may also be administered to patients in early stages of a disease or in the case of cancer patients, a patient in remission or with minimal residual disease. Application of the compositions to patients exhibiting symptoms are also within the scope of the invention. The composition may be administered via all the routes conventionally used or recommended for vaccines: including the parenteral, intradermal, intramuscular, subcutaneous or mucosal routes. In addition, the composition may be administered intraosseally, intrathecally, interperitoneally or intralaminally. In certain embodiments, the composition may also be administered intranodally or intratumorally.

The pharmaceutical priming vaccination composition of the present invention includes living, activated immune cells whereby at least a portion are T-cells. The composition may also include disease-related antigens. Disease-related antigens as referred to herein include antigens related to a disease causing pathogen, cells or lysates from a tumor or other antigens related to a disease. The activated Th1 memory cells used in the priming vaccine pharmaceutical compositions of the present invention are preferably derived from normal donor blood. Preferred methods for processing and production of cells suitable for use in the present invention are described by Har-Noy in U.S. Pat. Nos. 7,435,592 and 7,402,431 and pending US published patent application 2005/0191291 which are herein incorporated by reference in their entirety.

The number of Th1 memory cells used in the vaccine compositions can vary and may also depend on the route of administration. The priming and the activating composition generally have between about $1\times10^6$ cells and about $1\times10^{10}$ cells. Preferably, the compositions have between about $1\times10^6$ cells and about $1\times10^8$ cells. When the composition is administered intradermally or intratumorally, between about $1\times10^7$ cells and about $1\times10^9$ cells when the composition is administered interperitoneally, intraosseally or intrathecally and between about $1\times10^8$ cells and about $1\times10^{10}$ cells when the composition is administered intravenously. Compositions with Th1 memory cells outside of these ranges are also within the scope of this invention.

Patients that have been primed with a composition containing allogeneic Th1 memory cells will generally develop anti-alloantigen immunity. Subsequent injections of allogeneic cells can activate the pool of anti-alloantigen cells which can release the inflammatory cytokines necessary for disabling immune avoidance mechanisms.

In some embodiments, the priming vaccine composition can be administered to patients susceptible to diseases. These diseases may be diseases that occur often in elderly patients. The priming vaccine composition may be effective for patients susceptible to cancer or infectious diseases such as HIV/AIDS, Hepatitis B, Hepatitis C, herpes, tuberculosis and malaria. When the priming vaccine composition is administered to these patients, they develop an anti-alloantigen immunity. The patients' immune system can harbor a Th1 footprint that can be activated when necessary. In other words, the patients' immune system is in a standby mode and primed for a more effective Th1 response to an antigenic challenge. When the patient develops symptoms of a particular disease, activating vaccine compositions as described below can be administered.

In some embodiments, the priming vaccination can be administered to patients who have already had a disease such as cancer but are in remission. Patients in remission can sometimes have minimal residual disease (MRD). In MRD, patients can still have cancer cells but in amounts that are not clinically symptomatic. Overtime, the cancer cells can grow and lead to recurrence of the disease. Priming vaccinations that include the activated Th1 memory cells and one or more antigens from the initial cancerous cells can be administered to patients in remission to create a Th1 footprint. When the patient shows signs of a recurrence, activating vaccine compositions can be administered containing the activated Th1 memory cells and one or more of the disease-related antigens. Since the patient had been primed earlier, the resident anti-alloantigen memory can mount a response quickly to more effectively combat the full blown antigenic challenge.

The priming vaccine composition according to the present invention when administered to a patient in remission may be a composition intended for immunization against a single pathogen or cancer, i.e. it comprises one or more antigens from a single pathogen or cancer, or else it may be a composition intended for immunization against several different pathogens or cancers (this is then referred to as a vaccine combination).

The adjuvant action of the activated Th1 memory cells can be obtained when the activated Th1 cells and the disease-related antigens are combined prior to administration. Alternatively, the activated Th1 memory cells are administered separately form the disease-related antigen(s). Preferably, the activated Th1 memory cells are combined with the disease-related antigens prior to administration into the patient.

In order to maintain an inflammatory environment that is capable of disabling the ability of tumors and disease organisms to evade immune destruction, additional booster compositions of activated Th1 memory cells alone or formulated with antigen can be administered. Preferably the booster compositions can be made at least 3-7 days apart, and more preferably 7-14 days apart. Additional booster compositions can be administered to the patient as required on a monthly or yearly basis.

The antigen component of the pharmaceutical compositions includes one or more disease-related antigens. Any antigen source can be used in the formulation, for example these antigens can be sourced from living cells or organisms, the source material can be irradiation inactivated (or other inactivation method), used as whole cells or organisms or lysates therefrom. In particular, tumor cells or tumor cell lysates can serve as the cell source material for the antigens. The cell source material can be derived from autologous or allogeneic cell sources or from cell lines. Antigen sources are described in U.S. patent application Ser. No. 12/434,168 filed on May 1, 2009, incorporated herein by reference.

When the patient develops symptoms of a particular disease, activating vaccine compositions with activated Th1 memory cells and one or more sources of disease-related antigens are administered to the patient. The patient's immune system can be activated to produce a full scale Th1 response quickly and thus, a more effective response mounted against the antigens due to the anti-alloantigen immunity already present in the patient.

Activating vaccine compositions generally include allogeneic activated Th1 memory cells as described herein for the priming vaccine compositions. Preferably, the allogeneic Th1 memory cells administered to a patient in the activating composition are from the same source as the allogeneic Th1 memory cells used in the priming composition. The number of allogeneic activated Th1 memory cells administered to a patient can be about the same as the number of allogeneic cells administered in the priming compositions. Although the use of greater or lesser amounts of cells in the activating compositions are within the scope of the invention. Activating vaccine compositions may also include disease-related antigens as described herein. The allogeneic Th1 cells and the disease-related antigens maybe administered together as one activating vaccine composition. Alternatively, the allogeneic Th1 cells and the disease-related antigens can be administered as separate compositions.

Example

Mice—Five to six week old female Balb/c ($H-2^{d/d}$) and male C57BL/6 ($H-2^{b/b}$) mice were purchased from the Hebrew University-Hadassah Medical School Animal Facility, Jerusalem, Israel. All mice were kept under specific pathogen-free (SPF) conditions and given acidified water and food ad libitum. The study was approved by the Animal Ethical Committee of the Hebrew University Medical School. All mice were 6 to 8 weeks old when placed on experiment.

BCL1 Tumor Model—BCL1 is a spontaneous B-cell leukemia/lymphoma of Balb/c origin. The BCL1 tumor line is maintained in vivo by serial passages in Balb/c recipients. In these experiments, animals were infused intravenously through the tail vein with 2000 BCL1 cells on day 0 which is lethal in 100% of the mice. In some experiments, $1\times10^4$ BCL1 were implanted subcutaneously in the flank of Balb/c mice. BCL1 forms a rapidly growing solid tumor in this setting resembling lymphoma/plasmacytoma.

Preparation of Allogeneic Th1 Memory Cells—Allogeneic Th1 memory cells were prepared. Briefly, CD4+ cells were isolated from male C57BL/6 spleens and cultured for 6 days with anti-CD3 and anti-CD28-coated paramagnetic beads (CD3/CD28 T-cell Expander beads, Dynal/Invitrogen) at an initial bead:CD4 cell ratio of 3:1 and 20 IU/mL recombinant mouse (rm)IL-2, 20 ng/mL rmIL-7, 10 ng/mL rmIL-12 (Peprotech, New Jersey) and 10 µg/mL antimurine IL-4 mAb (Becton Dickenson) in RPMI 1640 media containing 10% FBS, penicillin-streptomycin-glutamine, non-essential amino acids (NEAA) (Biological Industries, Israel) and 3.3 mM N-acetyl-cysteine (NAC; Sigma) (complete media). After 6 days in culture, the CD4 cells were harvested and debeaded by physical disruption and passage over a magnet. These cells were either used fresh or stored in liquid nitrogen for future use. Prior to use, the cells were activated by incubation with anti-CD3/anti-CD28-coated nanobeads for 4 h in complete media.

Vaccinations—Mice were vaccinated with vaccine compositions suspended in 0.1 ml of HBSS or complete media. Inoculations were made either in alternating foot pads or in the skin layer of the shaved flank.

BCL1 tumor antigen preparations—BCL1 lysates and irradiated BCL1 cells were used as sources of tumor antigens. Batches of BCL1 lysate were derived from $1\times10^7$ BCL1 cells suspended in 2 mL of HBSS and lysed by 3 freeze (in −80° C. freezer)-thaw (37° C. water bath) cycles. Total cell disruption was microscopically validated using trypan blue staining. The lysate was mixed well to assure a homogenous solution and aliquoted into separate 0.2 ml doses. These doses were stored at −80° C. prior to use. Fresh BCL1 cells were irradiated at 20 Gy and used within an hour of treatment.

Monoclonal Antibodies—The following monoclonal antibodies (mAb) were used to surface phenotyping: anti-mCD4-PerCP-Cy5 (IgG2a); isotype control rat IgG2a-PerCP-Cy5.5; anti-mCD62L-APC (IgG2a); isotype control rat IgG2a-APC; anti-mCD45RB-PE (IgG2a); isotype control rat IgG2a-PE; anti-mCD8a-FITC (IgG2a); isotype control rat IgG2a-FITC; anti-mCD44-FITC (IgG2b); isotype Control rat IgG2b-FITC; anti-mCD154(CD40L)-PE (IgG); isotype control rat IgG-PE; anti-mCD25-APC (IgG1); isotype control rate IgG1-APC; anti-mCD3e-PerCP-Cy5.5 (IgG); isotype control Armeniam hamster IgG-PERCP-Cy5.5 all from eBioscience, Inc. (San Diego, USA).

ELISPOT Assay—Single cell suspensions of spleen cells from immunized mice were prepared. The cells were aliquoted so that $2\times10^6$ viable cells were plated in 2 ml of complete media in wells of a 24 well plate. The splenocytes in each well were pulsed with test antigens. The test antigens were prepared as freeze-thaw lysates suspended in complete media. Each well was pulsed with lysate from $1\times10^7$ cells: either BCL1, allogeneic Th1 cells or splenocytes from untreated syngeneic mice. The pulsed wells were cultured for 24 h at 37° C. in a humidified $CO_2$ incubator. After 24 h, the non-adherent cells were harvested, washed and counted. These cells were then plated in triplicate at 100,000 viable cells per well on pre-coated anti-IFN-γ and anti-IL-4 plates (eBioScience, San Diego, Calif.) and incubated for an additional 20 h in complete media supplemented with 20 IU/ml rmIL-2 (Peprotech). Fresh splenocytes from syngeneic mice activated with PHA were used as a positive control for each plate (data not shown). The plates were developed in accordance with the manufacturer's instructions and read on an automated image analysis system.

Cryoimmunotherapy tumor models—Two tumor models were used for the cryoimmunotherapy protocols, a bilateral solid tumor model and solid tumor with systemic disease model. The bilateral solid tumor model consisted of mice given subcutaneous injections of $1\times10^4$ BCL1 tumor cells bilaterally in the shaved flanks on day 0. For the solid tumor with systemic disease model, mice received a single subcutaneous inoculation of $1\times10^4$ BCL1 on day 0 on the left flank and also an intravenous infusion of 2000 BCL1.

Cryoablation—Anesthetized mice (ketamine-HCL, 100 mg/kg, i.p.) underwent cryoablation treatment by applying mild pressure for 10 seconds with frozen tweezers (which were kept in liquid nitrogen) to the tumor. Tumors were 16-25 $mm^2$ when treated. The ice ball covered the complete tumor mass. To ensure complete thawing of the treated area before vaccination, intratumoral treatments were administered after 1 hour.

Statistics—Two-way ANOVA was used to determine significant differences in cytokine levels, ELISPOT response frequencies and tumor volume changes. A P value of <0.05 was considered significant. Logrank and hazard ratio analysis was used to compare Kaplan-Meier survival curves (Graphpad Software; San Diego, Calif.). Animals that survived >60 days were censored from the analysis.

Immune response to BCL1 vaccination with or without adjuvant. (FIG. 1A and FIG. 1B) Balb/c mice (n=3) were vaccinated four times intradermally at weekly intervals with either freeze-thawed BCL1 tumor lysate (f/t BCL1) or irradiated BCL1 (irrad BCL1) without adjuvant (FIG. 1A) or mixed with $1\times10^3$ CD3/CD28 cross-linked allogeneic Th1 cells (allo Th1) as adjuvant (FIG. 1B). On the 5th week following the first inoculation, animals were sacrificed and their spleens harvested, single cell suspension cultures of splenocytes were pulsed with f/t BCL1 or f/t splenocytes from a naive Balb/c mouse as control. After 24 h, the non-adherent T-cells were removed and plated in triplicates at $1\times10^5$ cells per well of anti-IFN-γ and anti-IL-4-coated ELISPOT plates. After a culture of 20 h, IFN-γ and IL-4 spots were developed and counted by computer-assisted video image analysis. Each bar represents the mean spot number of triplicates+/−SE out of $10^5$ T-cells. Asterick (*) on FIG. 1A and FIG. 1B indicates significant difference (p<0.05) and n.s. indicates not significant (p>0.05) compared to control and between bracketed values (ANOVA 2-tailed test).

Figure 2A:
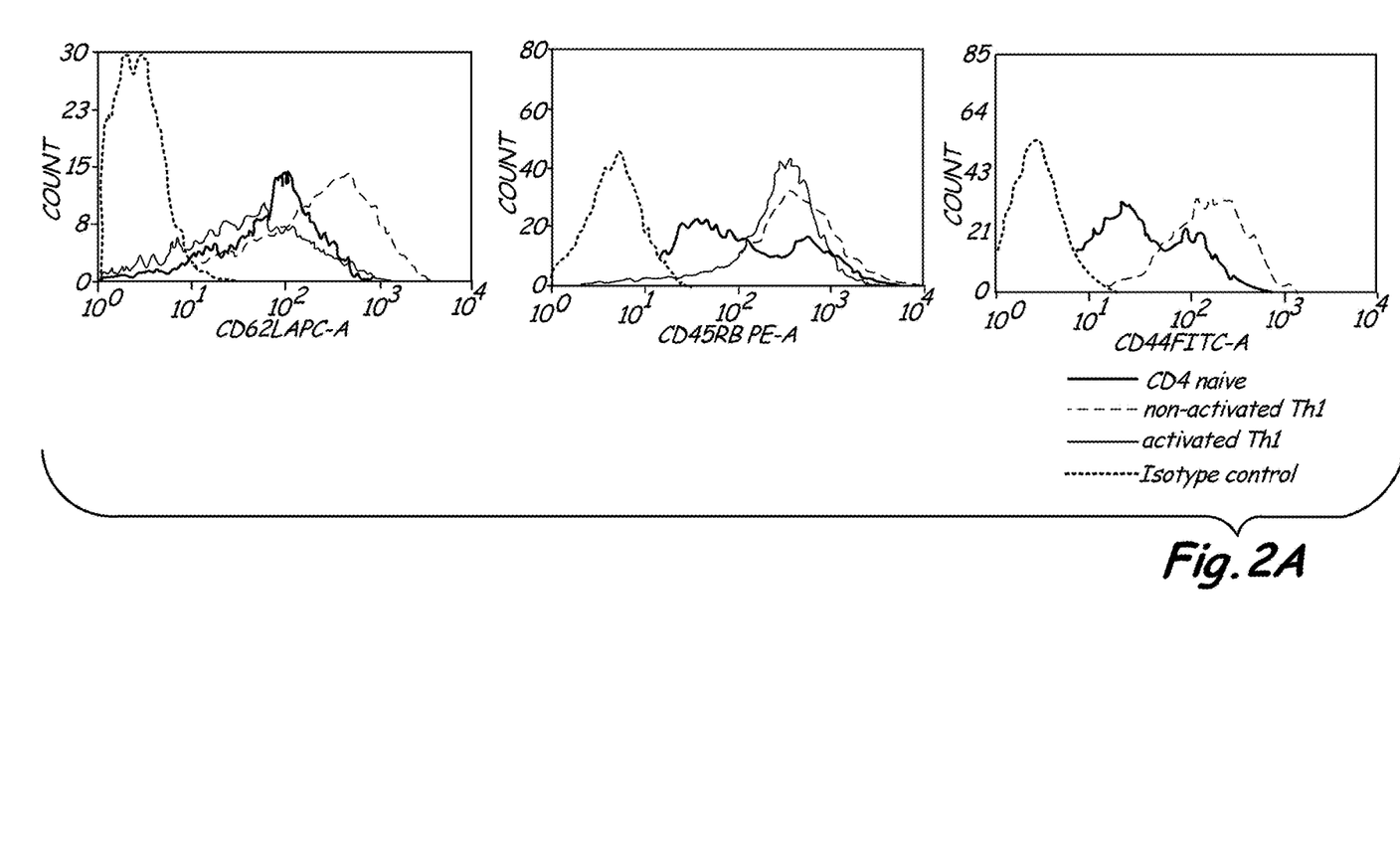
FIG. 2A shows plots of the phenotypic shift in CD45RB, CD62L and CD44 from Day 0 to Day 6.
Figure 2B:
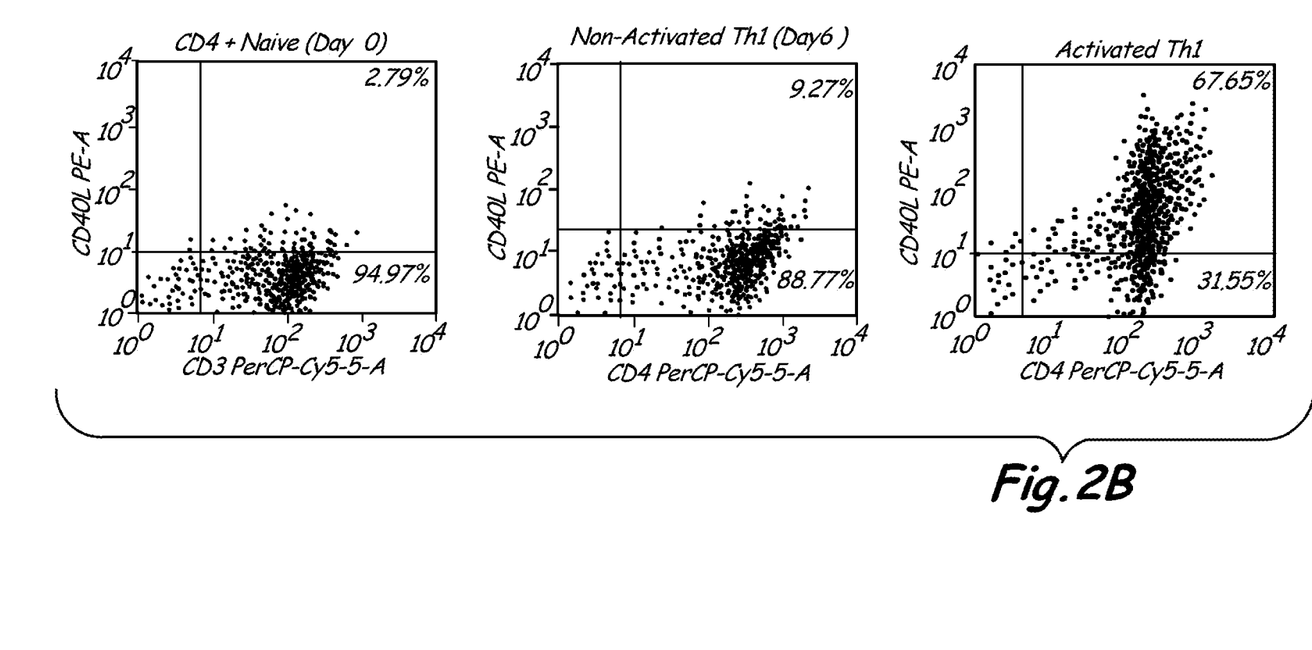
FIG. 2B shows plots of the phenotypic changes in the CD40L effector molecule expression in CD4+ cells placed in culture on Day 0, Day 6 and activated.
Figure 2C:
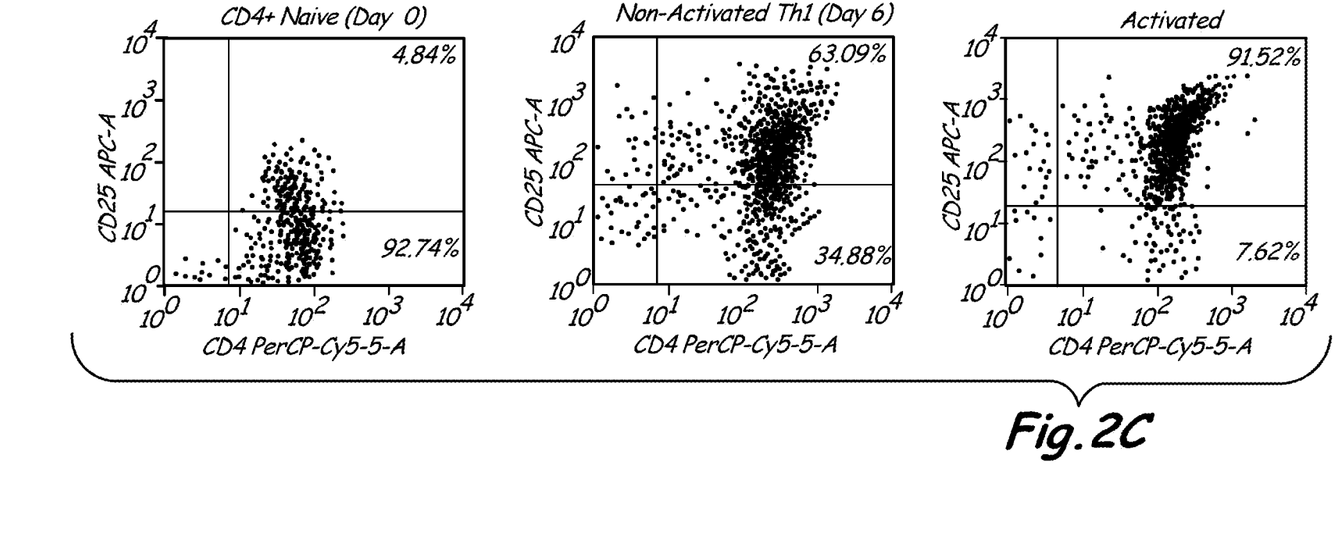
FIG. 2C shows plots of the phenotypic changes in the CD25 expression in CD4+ cells placed in culture on Day 0, Day 6 and activated.

Characterization of CD3/CD28 cross-linked Th1 cells. (FIG. 2A, FIG. 2B and FIG. 2C) C57BL/6-derived positively selected CD4+ T-cells were placed in culture on day 0 in cRPMI supplemented with rmIL-12, rmIL-7, rmIL-2 and a neutralizing anti-IL-4 mAb and activated with CD3/CD28 conjugated T-Cell Expanded beads (Dynal/Invirogen) at a 3:1 bead:cell ratio. The cells were split daily from day 3-6 and supplemented with additional T-cell Expander beads, rmIL-7, rmIL-2 and anti-IL-4 mAb. On day 6, the cells were harvested and activated with CD3/CD28 conjugated nanobeads. The phenotypic shift in CD45RB, CD62L and CD44 from Day 0 to Day 6 is shown in FIG. 2A. The black filled area represents the isotype control. The black line is the phenotype of Day 0 CD4+ cells. The gray filled area is the phenotype of day 6 cells prior to CD3/CD28 nanobead activation and the gray line represents the phenotype after CD3/CD28 nanobead activation. FIG. 2B shows the phenotypic changes in the CD40L effector molecule expression in CD4+ cells placed in culture on day 0 compared to Day 6 harvested cells before and after CD3/CD28 nanobead activation. Only the activated cells expressed significant amounts of this effector molecule. FIG. 2C represents the phenotypic change in CD25 expression in Day 0 CD4+ cells compared to Day 6 cells before and after CD3/CD28 nanobead activation. The phenotype of the activated day 6 cells was CD4+, CD62Llo, CD45RBhi, CD44hi, CD40L+, CD25+.

Figure 3A:
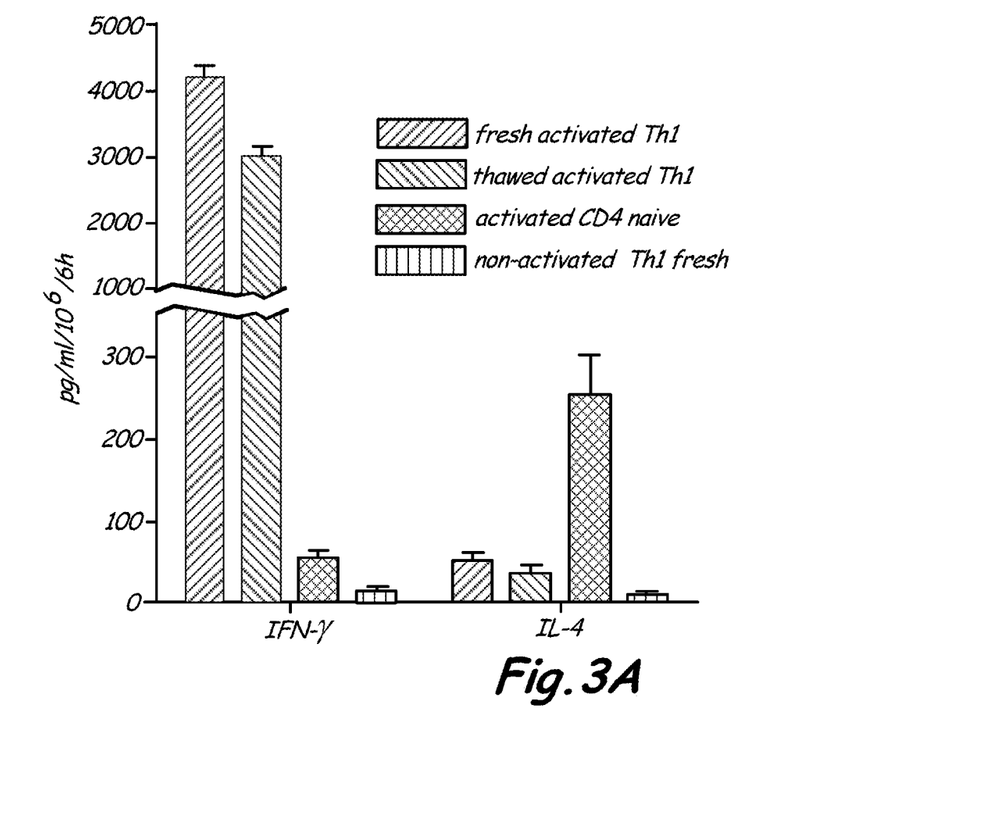
FIG. 3A is a bar graph of the cytokine production of CD3/CD28 cross-linked Th1 memory cells.

Cytokine production (FIG. 3A) and immunogenicity (FIG. 3B) of CD3/CD28 cross-linked Th1 memory cells. IFN-□ and IL-4 cytokine production was analyzed in supernatants from 6 h cell cultures by ELISA. CD4 cells positively selected from C57BL/6 cultured for 6 days in the presence of IL-12 (day 1-3 only), IL-7 and IL-2 expanded 60-100-fold and differentiated to CD45RBhi, CD44hi effector/memory cells. These cells were harvested on Day 6, washed and reactivated with CD3/CD28 nanobeads, cultured for 6 h and the supernatants collected for analysis of by ELISA (FIG. 3A: Fresh activated Th1). These results were compared to supernatants from 6 h cultures of the same Day 6 harvested cells that were first frozen in liquid nitrogen and then later thawed and activated with CD3/CD28 nanobeads (FIG. 3A: thawed activated Th1). For comparison, supernatants from a sample of positively selected CD4 cells (the same that were placed in culture on Day 0) were activated with CD3/CD28 T-cell Expander Beads at a 3:1 bead:cell ratio and cultured for 6 h (FIG. 3A: CD4 naïve). Supernatants from Day 6 harvested cells were also cultured for 6 h without CD3/CD28 activation (FIG. 3A: nonactivated Th1 fresh).

Figure 3B:
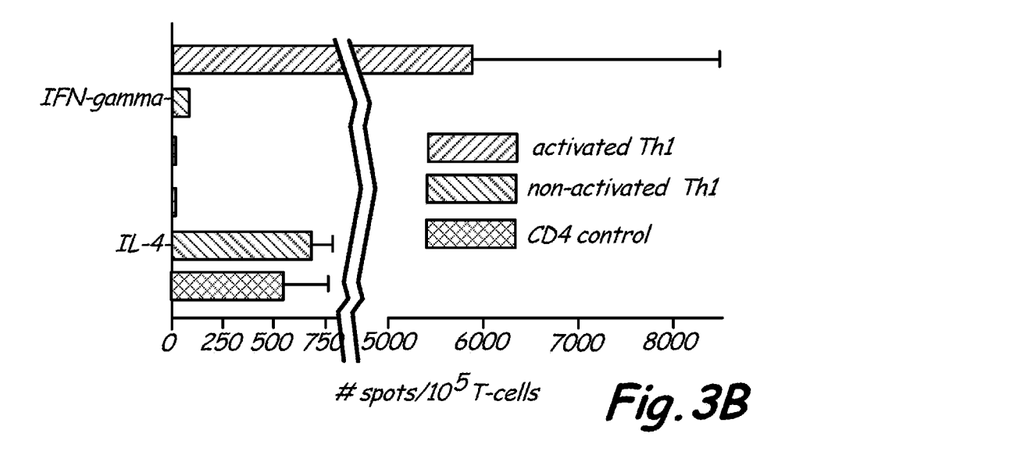
FIG. 3B is a bar graph of the immunogenicity of CD3/CD28 cross-linked Th1 memory cells.

The immunogenicity of these cell compositions were tested by ELISPOT (FIG. 3B). $1 \times 10^4$ fresh activated Th1 cells, fresh non-activated Th1 cells or positively selected CD4 cells (control) derived from C57BL/6 mice were inoculated intradermally in allogeneic Balb/c mice once a week for 4 weeks. During the 5th week, the mice (n=3) were sacrificed, spleens removed and single cell splenocytes cultures established. The cultures were pulsed with freeze/thawed lysates of CD57BL/6 splenocytes and cultured for 24 h. The non-adherent T-cell fraction was then harvested, washed, and $1 \times 10^5$ cells were transferred to anti-IFN-γ or anti-IL-4 coated ELISPOT plates in triplicate and cultured another 20 h in the presence of 20 IU rmIL-2. Each bar represents the mean spot number of triplicates±SE.

Protective vaccination and tumor challenge. Kaplan-Meier survival curves of Balb/c mice vaccinated against BCL1 tumor (n=8 for each group). (FIG. 4) All mice were infused i.v. with 2000 cells of BCL1 on day 0. Prior to tumor challenge, mice were inoculated i.d. on day −22, day −15, day −8 and day −1 with either media alone (control), $1 \times 10^4$ allogeneic CD3/CD28 cross-linked Th1 cells (Th1 alone), $1 \times 10^4$ allogeneic CD3/CD28 cross-linked Th1 cells mixed with irradiated BCL1 (irrad BCL1+Th1) or $1 \times 10^4$ allogeneic CD3/CD28 cross-linked Th1 cells mixed with freeze/thawed BCL1 tumor lysate (f/t BCL1+Th1). The median survival of the control mice was 21 days. Vaccination with irrad BCL1 alone (median survival=20.5 days) or f/t BCL1 alone (median survival=20.0 days) did not significantly affect survival compared to control. The Th1 alone pretreatment significantly extended survival to a mean of 24 days (hazard ratio=3.14). Vaccination with irrad BCL1 with Th1 as an adjuvant did not have a significant effect on survival (mean survival=22 days). Mixing f/t BCL1 with Th1 resulted in 50% of the mice surviving lethal tumor challenge and resulted in a median survival of 46 days (hazard ratio=6.08).

Therapeutic vaccination. Kaplan-Meier Survival Curves of Balb/c Mice (n=6 per group) infused with 2000 BCL1 iv on day 0. (FIG. 5) Mice were given id injections of either $1 \times 10^4$ allogeneic CD3/CD28 cross-linked Th1 memory cells alone (Th1) or f/t lysate of $1 \times 10^6$ BCL1 mixed with Th1 (f/t BCL1+Th1) i.d. on days 1, 8 and 15. Control mice survived a mean of 19.5 days. Mice vaccinated with Th1 alone survived significantly longer than control with a mean of 26 days (logrank: p=0.001; hazard ratio: 3.981). Mice vaccinated with f/t BCL1+Th1 also survived significantly longer than control mice with a mean survival of 34 days (logrank: p=0.001; hazard ratio: 3.981), which was not significantly different than the Th1 alone group.

Figure 6:
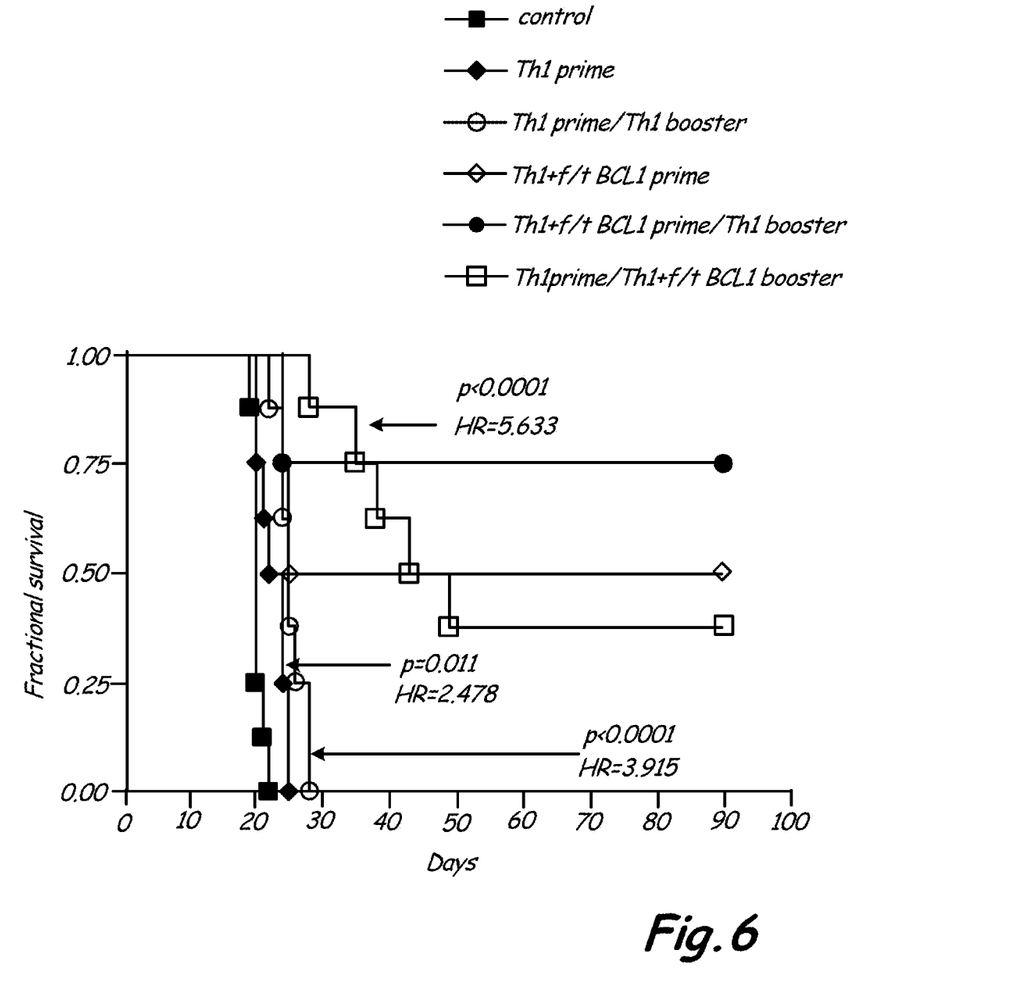
FIG. 6 is a plot showing the results from priming and a therapeutic booster.

Prime with therapeutic booster. Kaplan-Meier survival curves of Balb/c mice vaccinated against BCL1 tumor (n=8 for each group). (FIG. 6) All mice were infused iv with 2000 cells of BCL1 on day 0. Prior to tumor challenge, mice were primed by inoculation i.d. on day −22, day −15, day −8 and day −1 with either media alone (control), $1 \times 10^4$ allogeneic CD3/CD28 cross-linked Th1 cells (Th1) or $1 \times 10^4$ Th1 mixed with freeze/thawed BCL1 tumor lysate (Th1+f/t BCL1 prime). On day 7, some mice were administered therapeutic booster inoculations i.d. with either Th1 alone or Th1 mixed with f/t BCL1. Control mice survived a median of 20 days. Vaccination with Th1 alone resulted in significant survival extension to a median of 23 days (logrank: p=0.011;

hazard ratio: 2.478). Vaccination with Th1 alone followed by a Th1 booster resulted in significant survival advantage (median survival=25 days) compared to control (logrank: p<0.0001; hazard ratio=3.915) and significant survival compared to Th1 alone (logrank: p=0.03; hazard ratio=2.337). Mice primed by vaccination with f/t BCL1 with Th1 as adjuvant (Th1+f/t BCL1 prime) resulted in median survival of 57.5 days with 50% of mice surviving lethal challenge. Mice primed with Th1+f/t BCL1 and administered a Th1 booster had 75% survival lethal challenge. Mice primed with Th1 cells alone and administered a therapeutic booster injection with f/t BCL1+Th1 had a significant survival advantage compared to control with median survival of 46 days (logrank: p<0.0001; hazard ratio=5.633) and 37.5% of mice surviving lethal challenge.

Figure 7A:
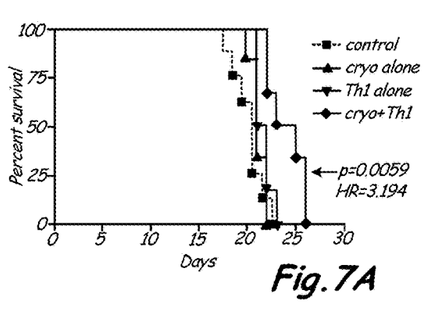
FIG. 7A is plot showing the response in a cryoablation systemic tumor model.
Figure 7B:
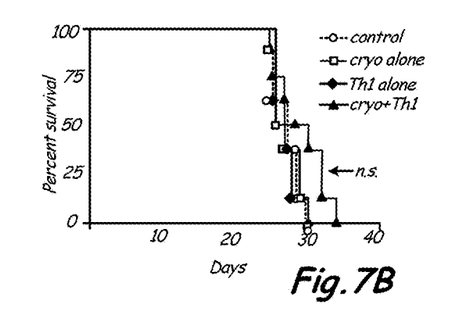
FIG. 7B is a plot showing the response in a cryoablation solid tumor model.
Figure 7C:
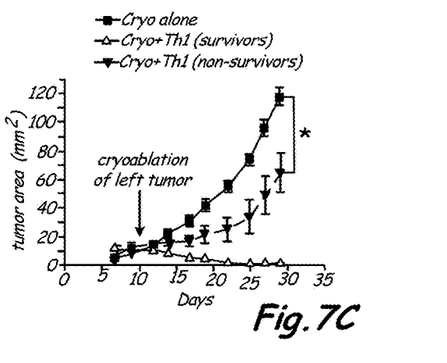
FIG. 7C is a plot showing the response in a solid tumor contralateral (right) tumor growth.

Solid tumor and systemic tumor response to cryoimmunotherapy. In the solid tumor model, Balb/c mice were administered subcutaneous inoculations of $1 \times 10^4$ BCL1 tumor cells bilaterally on the shaved flanks on day 0. In the systemic tumor model, Balb/c mice were administered inoculations of $1 \times 10^4$ BCL1 tumor cells on the left flank and 2000 BCL1 intravenously through the tail vein on day 0. The Kaplan-Meier survival curves of systemic tumor model (FIG. 7A) and solid tumor model (FIG. 7B) mice (n=8 each group) treated on day 14 with cryoablation of all observable tumor of the left tumor mass either alone (cryo alone) or with intratumoral allogeneic CD3/CD28 cross-linked Th1 memory cells (Th1) (cryo+Th1) or with intratumoral Th1 cells alone without cryoablation (Th1 alone). Control mice survived a median of 21 days in the systemic model and 28.5 days in the solid tumor model. The cryo+Th1 treatment resulted in significant survival advantage (logrank: p=0.0059; hazard ratio=3.194) in the systemic model. The survival advantage in the solid tumor model was not significant (n.s.). The same experiment was repeated with the addition of a $1 \times 10^5$ intravenous infusion of Th1 on day 7 for all mice. FIG. 7C shows the tumor growth curves of the contralateral untreated tumor masses for mice treated with this protocol. 40% of the mice treated with cryo+Th1 were cured of disease. The growth of contralateral tumor was significantly suppressed (p<0.01) in the other 60% of mice that eventually succumbed to disease. In the systemic tumor model (FIG. 7D), Kaplan-Meier survival curves are shown. Mice treated with intratumoral Th1 cells alone survived a mean of 28 days, which was significantly longer than control mice which survived a mean of 19 days (logrank: p<0.0001; hazard ratio=4.291). 40% of mice treated with cryo+Th1 survived >90 days.

Results

BCL1 Immunogenicity—The native immune response to BCL1 vaccination in Balb/c mice was characterized to serve as a baseline in which to analyze the biological effects of adding an adjuvant. Since BCL1 has been continuously passaged in-vivo for many years that the current BCL1 clone would prove to be non-immunogenic when administered to syngeneic Balb/c mice without an adjuvant due to "immunoediting".

The immunogenicity of two vaccine preparations of BCL1, either irradiated whole BCL1 (irrad BCL1) or a freeze-thawed lysate of BCL1 (f/t BCL1) were tested without adjuvant (FIG. 1A) or mixed with $1 \times 10^3$ CD3/CD28 cross-linked allogeneic Th1 cells (allo Th1) as adjuvant (FIG. 1B). The "danger hypothesis" predicts that the f/t BCL1 lysate preparation would be more immunogenic than the irrad BCL1 preparation. To test the immunogenicity of f/t BCL1 and irrad BCL1 preparations they were each administered intradermally (i.d.) to Balb/c mice in 0.2 ml of HBSS once a week for 4 weeks.

Figure 1A:
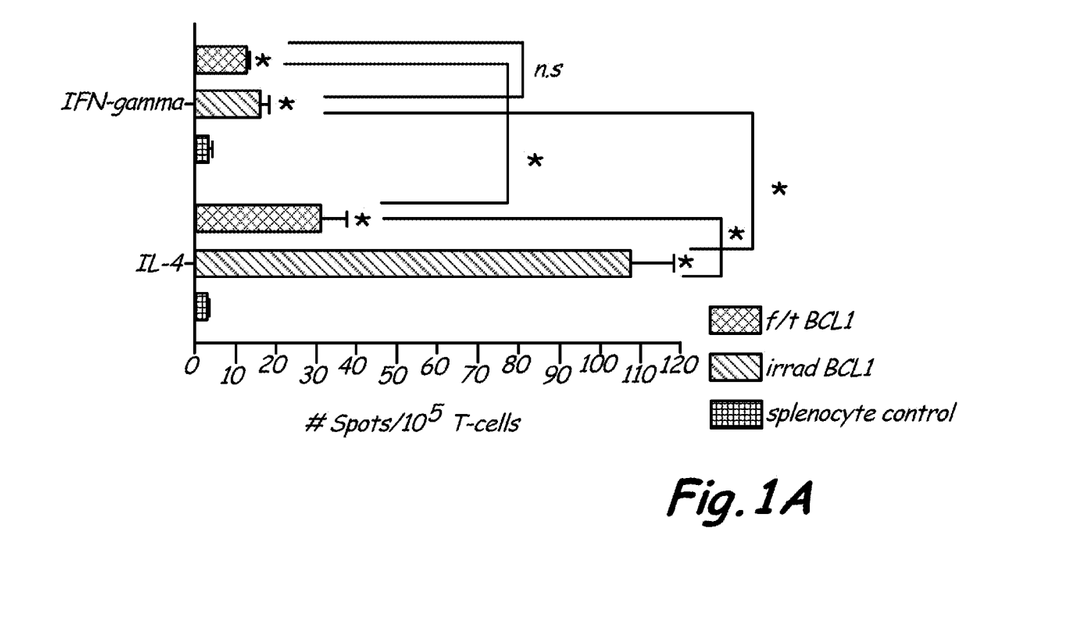
FIG. 1A is a bar graph showing the immune response to BCL1 without an adjuvant.
Figure 1B:
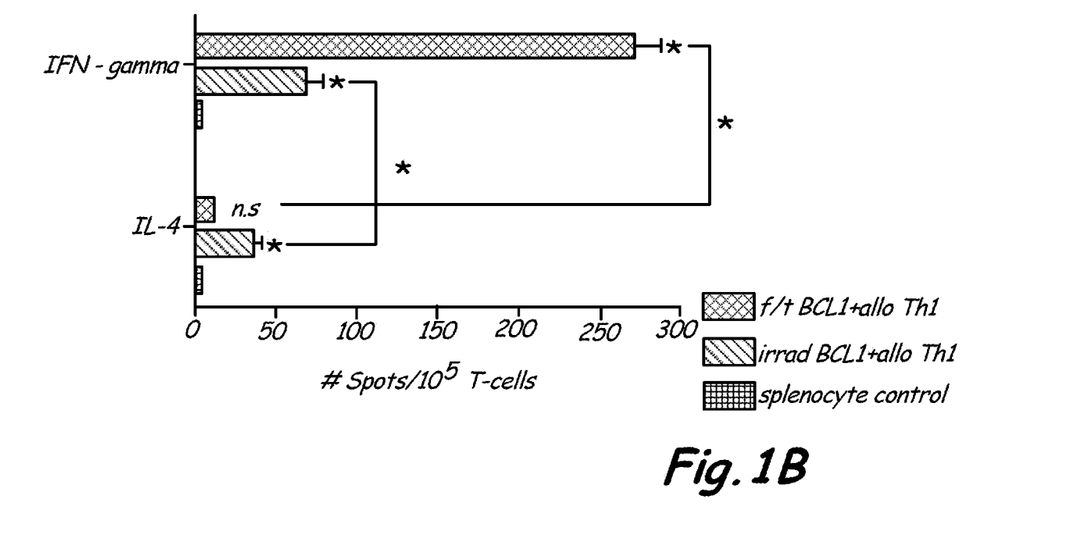
FIG. 1B is a bar graph showing the immune response to BCL1 with an adjuvant.

Vaccination with both irrad BCL1 and f/t BCL1 without adjuvant were able to elicit significant tumor-specific immune responses (see FIG. 1A). The mean frequency of tumor-specific T-cells (IL-4+IFN-γ spots) was 1/64 after vaccination with irrad BCL1, which was significantly greater (3.5-fold) than the mean frequency of 1/227 after f/t BCL1 vaccination. Both vaccination protocols resulted in significantly greater frequencies of responding T-cells compared to the control mean frequency of 1/3333 (p<0.001).

Both vaccine preparations caused tumor-specific T-cell responses biased to Th2 (IL-4). T-cell IL-4 mean frequency response to irrad BCL1 vaccination was 1/93 and the IFN-γ response was significantly lower (p<0.001) at 1/208. The mean frequency of IL-4 responders in f/t BCL1 vaccinated mice was 1/322 which was significantly higher (p<0.01) than the IFN-γ mean response frequency of 1/769. The mean frequency of IFN-γ responders in irrad BCL1 vaccinated mice compared to f/t BCL1 vaccinated mice were not significantly different.

None of the mice vaccinated with irrad BCL1 or f/t BCL1 were able to survive a lethal challenge of 2000 BCL1 cells administered intravenously through the tail vein (See FIG. 4), indicating the significant immune responses to both BCL1 vaccination protocols were not protective.

Characterization of CD3/CD28 cross-linked Th1 Memory cells—The C57BL/6-derived CD3/CD28 cross-linked Th1 memory cells were first characterized for the surface phenotype (FIG. 2A-C), cytokine production profile (FIG. 3A) and immune response after 4 weekly i.d. injections in allogeneic Balb/c mice (FIG. 3B).

The surface expression of CD62L, CD45RB, CD44, CD25 and CD40L was analyzed to characterize the differentiation of cells over the 6 day culture by FACS of day 0 CD4+ source cells and compared the staining patterns to the same cells harvested after 6 days in culture before and after activation by CD3/CD28 cross-linking. Results are shown in FIG. 2A.

The day 0 positively selected CD4+ cells from splenocytes were stained $CD62L^{hi}$, $CD44^{hi}$ but converted from a $CD62L^{hi}$ phenotype to a $CD62L^{lo}$ phenotype. Therefore, the day 6 CD3/CD28 cross-linked cells expressed a phenotype of CD4+, $CD62L^{lo}$, $CD45RB^{hi}$, $CD44^{hi}$.

Phenotypically, mouse memory cells are normally $CD62L^{lo}$, $CD45RB^{lo}$, $CD44^{hi}$. The $CD62L^{lo}$, $CD45RB^{lo}$, $CD44^{hi}$ phenotype of cells produced by our culture method express the same phenotype as memory/effector cells that have been previously associated with autoimmune disease and allograft rejection.

Activation by CD3/CD28 cross-linking of day 6 cells for 4 h caused a significant increase in the number of cells expressing CD40L from 9.27% to 67.65% (FIG. 2B) which correlated with an increase in cells expressing CD25 from 63.09% to 91.52% (FIG. 2C).

These CD3/CD28-activated $CD4^+$, $CD62L^{lo}$, $CD45RB^{hi}$, $CD44^{hi}$, $CD40L^+$, $CD40L^+$, $CD25^+$ memory/effector cells (n=6 batches) were tested for cytokine production after activation by CD3/CD28 cross-linking of fresh day 6 harvested cells or day 6 harvested cells that had been frozen in liquid nitrogen, thawed and activated. Activated Day 0 CD4+ cells and non-activated fresh harvested Day 6 cells were included for comparison (see FIG. 3).

Fresh activated CD4+ memory/effector cells expressed substantial amounts of IFN-γ (4210±169.7 pg/ml/6 h) and negligible IL-4 (52.33±6.8 pg/ml/6 h) and thus these cells are referred to as Th1 memory cells. When these Th1 memory cells are frozen in liquid nitrogen prior to activation and later thawed and activated, they maintain the Th1 phenotype but express approximately 29% less IFN-γ and IL-4 than the fresh cells (2985±173.5 pg/ml/6 h of IFN-γ and 37.2±6.95 pg/ml/6 h of IL-4). Non-activated Th1 memory cells produced negligible amounts of cytokines (13±6.7 pg/ml/6 h IFN-γ; 8.8±3.6 pg/ml/6 h IL-4). The source CD4+ cells isolated by positive selection from a single cell suspension of normal C57BL/6 splenocytes produced cytokines upon activation with CD3/CD28-conjugated microbeads with a Th2 bias (254±50.2 pg/ml/6 h IL-4; 53.5±11.4 pg/ml/6 h IFN-γ).

These data demonstrate that the culture conditions cause CD4+ naïve cells with a Th2 bias to differentiate to strongly polarized Th1 memory/effector cells which express CD40L upon CD3/CD28 cross-linking and express an unusual $CD62L^{lo}$, $CD45RB^{hi}$, $CD44^{hi}$ memory phenotype.

Immune Response to Allogeneic CD3/CD28 Cross-linked Th1 Memory Cells—To characterize the potential of allogeneic CD3/CD28 cross-linked Th1 memory cells to provide adjuvant activity for promotion of Type 1 immunity, a study was conducted to determine if the C57BL/6 derived Th1 memory cells were able to elicit Type 1 immunity to their own alloantigens in allogeneic Balb/c hosts. Mice were administered $1 \times 10^4$ CD3/CD28 cross-linked Th1 memory cells or $1 \times 10^4$ Th1 memory cells without CD3/CD28 cross-linking i.d. in 0.1 ml of cRPMI, inoculation of cRPMI along was used as a control. Mice (n=6) were inoculated once weekly for four weeks.

During the 5$^{th}$ week after the first vaccination, the mice were sacrificed and spleens were removed and single cell suspensions were prepared for ELISPOT analysis as previously. Results are shown in FIG. 3B.

Vaccination with allogeneic CD4 cells (Day 0) alone resulted in a base line allogeneic immune response means frequency (IFN-γ+IL-4) of 1/348 T-cells. Allogeneic Th1 cells (Day 6) without CD3/CD28 cross-linking resulted in a response mean frequency of 1/268 T-cells, which was not significantly different than the CD4 cells alone. However, CD3/CD28 cross-linking of the allogeneic Th1 cells resulted in a mean frequency of 1/34 alloantigen-specific T-cells, which was significantly greater than the response frequency of allogeneic CD4 cells and non-activated allogeneic Th1 cells ($p<0.0001$).

The immune response to allogeneic CD4 cells and non-activated allogeneic Th1 memory cells resulted in skewed Th2 immunity, while the CD3/CD28 cross-linked allogeneic Th1 memory cells elicited a strongly polarized Th1 response. CD4 cell vaccination resulted in a mean frequency of 1/181 IL-4 producing T-cells, which was significantly greater ($p<0.0001$) than the mean frequency of 1/4167 IFN-γ producing T-cells. Non-activated allogeneic Th1 memory cells elicited a mean frequency of 1/147 IL-4 responding T-cells, which was significantly greater ($p<0.0001$) than the mean frequency of 1/1587 IFN-γ responding T-cells. The syngeneic splenocyte control did not elicit a detectable adaptive immune response (results not shown).

Protective Vaccination and Challenge—In order to determine if allogeneic Th1 cells could serve as an adjuvant to protect mice from a lethal challenge of BCL1 tumor, vaccine mixtures were prepared of either freeze/thawed BCL2 lysate (f/t BCL1) or irradiated BCL1 cells (irrad BCL1) used alone (control) or mixed with $1\times10^4$ allogeneic Th1 cells. Allogeneic Th1 cells alone without a source of tumor antigen were used as a control. Mice (n=8 in each group) received 4 i.d. inoculations of the vaccine preparations at weekly intervals on days −22, −15, −8 and −1. Media alone injections were used as a control. On day 0, all vaccinated mice received a lethal i.v. challenge of 2000 BCL1 cells.

Figure 4:
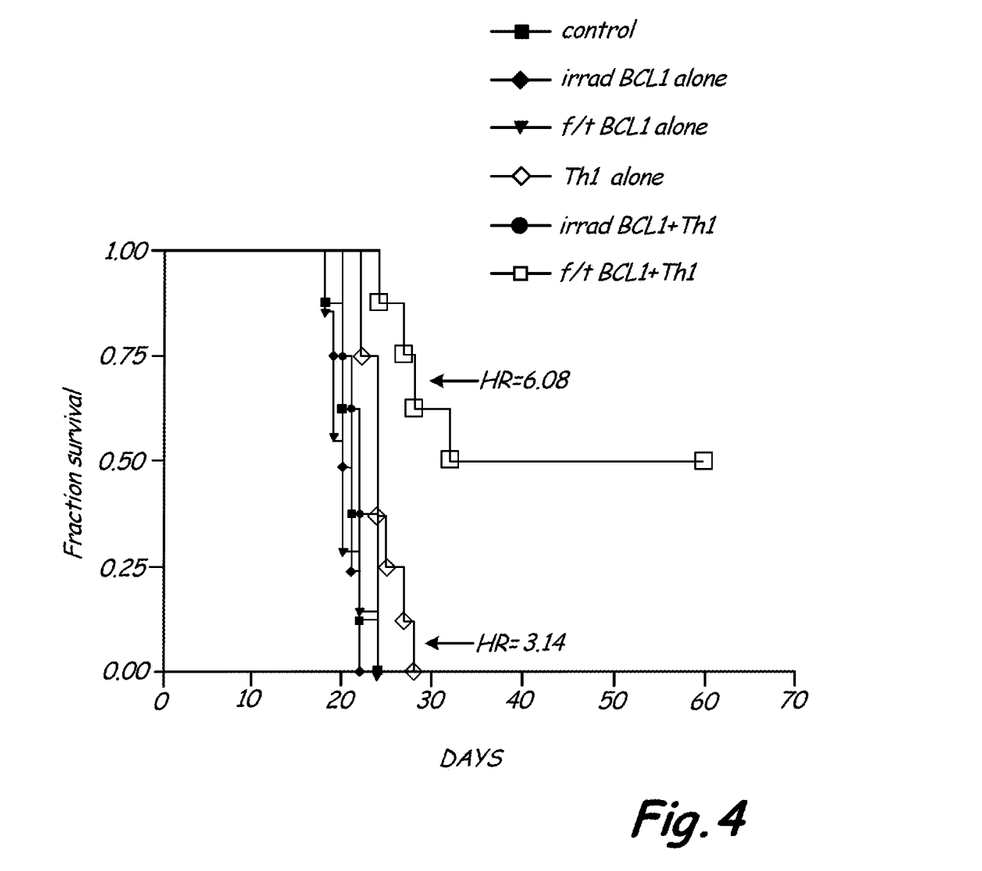
FIG. 4 is a plot showing the protective vaccination capabilities of allogeneic activated Th1 memory cells and response to tumor challenge.

Mice were followed for survival (see FIG. 4). The median survival of the media alone control mice was 21 days. Vaccination with either irrad BCL1, f/t BCL1 or allogeneic Th1 alone did not result in protection from tumor challenge. Interestingly, the allogeneic Th1 alone vaccination, while not protective, significantly extended survival of challenged mice to a mean of 24 days (hazard ratio=3.14). Vaccination with a composition of irrad BCL1+TH1 cells did not affect survival (median survival=22 days) and did not provide protection. Vaccination with f/t BCL1+Th1 cells resulted in a median survival of 46 days (hazard ratio=6.08) with 50% of the mice surviving lethal tumor challenge.

Therapeutic Vaccine Protocol—The above data demonstrated the protective effects of vaccination with f/t BCL1 and allogeneic CD3/CD28 cross-linked Th1 memory cells used as an adjuvant in animals that were vaccinated when they were tumor free and then challenged with a lethal dose of tumor. In order to determine if this protective effect could also provide a therapeutic effect, vaccination protocols were investigated in mice with pre-existing tumors.

Figure 5:
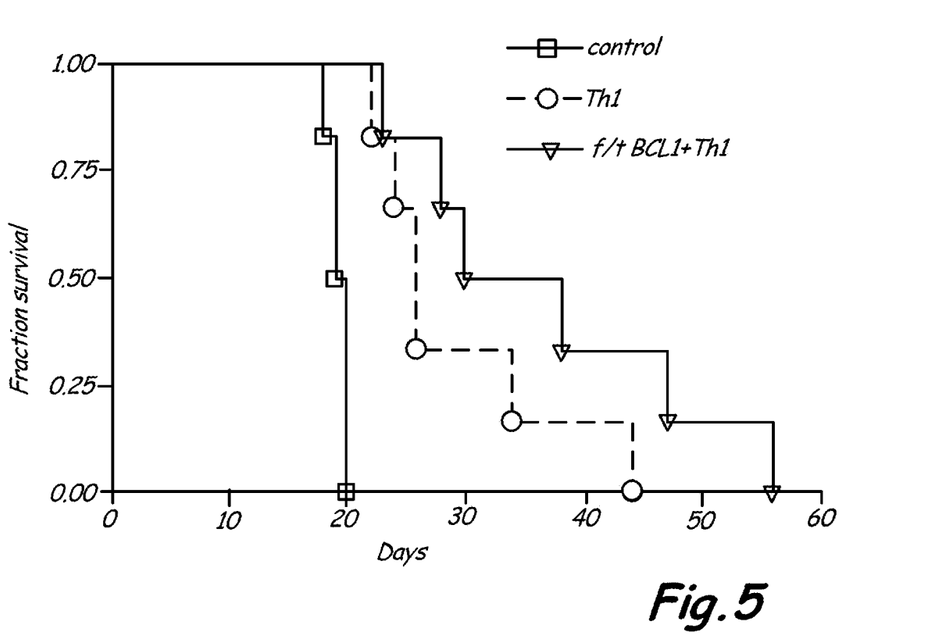
FIG. 5 is a plot showing the therapeutic vaccination capabilities of allogeneic activated Th1 memory cells.

The previous protective vaccination protocol included 4 weekly i.d. inoculations (28 days) followed by tumor challenge on day 35. This vaccination schedule could not be translated to the therapeutic setting in our model, as mice succumb to disease 19-22 days after lethal BCL1 infusion. Therefore, mice (n=6 each group) received a lethal dose of 2000 BCL1 cells intravenously on day 0 and therapeutic vaccinations of either $1\times10^4$ allogeneic CD3/CD28 cross-linked Th1 memory cells alone (Th1) or f/t lysate of $1\times10^6$ BCL1 mixed with allogeneic Th1 (f/t BCL1+Th1) i.d. on days 1, 8 and 15. Media alone inoculations on the same schedule served as control. Results are shown in FIG. 5.

Control mice survived a mean of 19.5 days. Interestingly, mice vaccinated with Th1 alone without any source of tumor antigen survived significantly longer than control with a mean of 26 days (logrank: p=0.001; hazard ratio: 3.981). Mice vaccinated with f/t BCL1+Th1 also survived significantly longer than control mice with a mean survival of 34 days (logrank: p=0.001; hazard ratio: 3.981), but this was not significantly different than the allogeneic Th1 alone group. No mice were cured with either of these therapeutic vaccine protocols.

Prime and Therapeutic Booster Vaccination—Since no mice were cured in the therapeutic vaccine protocols, the 19-22 day lifespan of mice infused with BCL1 tumors was not sufficient time to develop an adoptive immune response that could overwhelm the rapidly growing tumor. Therefore, tests were run to determine whether mice that were primed with allogeneic Th1-containing vaccinations prior to tumor challenge would respond better to therapeutic vaccination. In these experiments, mice were primed by i.d. inoculations on day −22, day −15, day −8 and day −1 with either media alone (control), $1\times10^4$ allogeneic CD3/CD28 cross-linked Th1 cells (Th1) or $1\times10^4$ Th1 mixed with freeze/thawed BCL1 tumor lysate (Th1+f/t BCL1 prime). All mice were infused with 2000 BCL1 on day 0. On day 7, some mice were administered i.d. therapeutic booster inoculations of either $1\times10^4$ Th1 alone or $1\times10^4$ Th1 mixed with f/t BCL1. Results are shown in FIG. 6.

Control mice survived a median of 20 days. Priming with Th1 alone again resulted in significant survival extension to a median of 23 days (logrank: p=0.011; hazard ratio: 2.478). Priming with Th1 alone followed by a Th1 therapeutic booster resulted in significant survival advantage (median survival=25 days) compared to control (logrank: p<0.0001; hazard ratio=3.915) and significant survival compared to Th1 prime alone (logrank: p=0.03; hazard ratio=2.337). Mice primed by vaccination with f/t BCL1 with Th1 as adjuvant (Th1+f/t BCL1 prime) had median survival of 57.5 days with 50% of mice surviving lethal challenge, the same result obtained in our previous experiment (see FIG. 4). Mice primed with Th1+f/t BCL1 and administered a Th1 therapeutic booster had 75% survival after a lethal challenge. Mice primed with Th1 cells alone and administered a therapeutic booster injection with f/t BCL1+Th1 had a significant survival advantage compared to control with median survival of 46 days (logrank: p<0.0001; hazard ratio+5.633) and 37.5% of mice surviving lethal challenge.

The shape of the Kaplan-Meier survival curve for the Th1 prime/Th1+f/t BCL1 booster group was different when compared to other groups that also resulted in mice cured after lethal BCL1 injection. The 50% of mice that did not survive after Th1+f/t BCL1 prime and the 25% that did not survive lethal challenge from the Th1+f/t BCL1 prime/Th1 booster group showed immediate signs of leukemia (palpable splenomegaly and significant weight gain) and succumbed to the disease very early at a mean of 24 days. By contrast, the Th1 prime+f/t BCL1 treatment group contained a subset of mice (62.5%) also with obvious leukemia but that survived significantly longer than control mice and a separate subset (37.5%) that were apparently cured and never showed signs of leukemia.

Cryoimmunotherapy—In order to try to further improve the efficacy of therapeutic vaccination, it was hypothesized that in-situ tumor death by necrosis would provide a more potent adaptive immune response than our other freeze-thawed lysate preparations. Neurotically killed cells are known to activate endogenous signals of distress responsible for the recruitment and maturation of DC, stimuli that would note be generated by healthy or apoptotically dying cells and may be missing from our lysate preparations. Further, exposure of immature DC to these stimuli provides maturation signals, critical for the initiation of local and systematic Th1 immunity.

In order to cause in-situ death by necrosis, a cryoablation protocol was used. Cryoablation surgery is a technique that can be translated to the clinic and has been shown to be a well-aimed and controlled procedure capable of inducing tissular necrosis. Cryoablation has been known to elicit an antigenic stimulus (capable of generating a specific immunologic response against autologous antigens of the frozen tissue).

Two tumor models were established where subcutaneous tumors were available for cryoblation. In the solid tumor model, Balb/c mice were administered subcutaneous inoculations of $1 \times 10^4$ BCL1 tumor cells bilaterally on the shaved flanks on day 0. In the systemic tumor model, Balb/c mice were administered inoculous of $1 \times 10^4$ BCL1 tumor cells on the left flank and 2000 BCL1 Intravenously through the tail vein on day 0. The left tumor of these animals (n=8 per group) were then treated on day 14 after the solid tumors had grown to an area>16 $mm^2$ with cryoblation alone, cryoblation with intratumoral $1 \times 10^3$ allogeneic CD3/Cd28 cross-linked Th1 memory cells (Th1), Th1 cells alone or intratumoral complete media alone as control. The results are shown in FIGS. 7A and 7B.

In the systemic tumor model (FIG. 7A), the mean survival of control mice was 21 days. Survival of mice treated with cryoblation alone and Th1 alone was not different than control. However, the combination of cryoblation with intratumoral Th1 treatment resulted in significantly extended survival to a mean of 28.5 days (logrank: p=0.0057; hazard ratio: 3.194). In the solid tumor model (FIG. 7B), the mean survival of control mice was 28 days. None of the treatments tested in this model provided a significant survival advantage.

Because the cryoblation protocol did not result in any mice cured as result of the treatment, we modified the treatment to include a $1 \times 10^5$ intravenous infusion of allogeneic Th1 on day 7 for all mice. It was previously shown that intravenous infusion of $1 \times 10^5$ allogeneic Th1 cells on day 7 caused a significant survival advantage in mice lethally injected with BCL1 on day 0. It was hypothesized that this treatment would provide more time for a potentially curative adaptive immune response to develop and thus affect the survival of mice undergoing cryoimmunotherapy. Further, this treatment would prime for alloantigen immunity, shown earlier (FIG. 6) to provide a survival advantage.

Figure 7D:
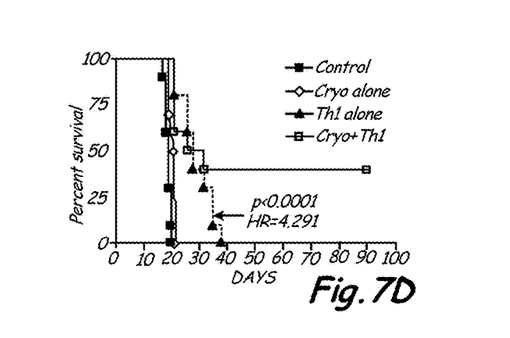
FIG. 7D is a plot showing systemic tumor model survival.

The results of these studies are shown in FIG. 7C (solid tumor model) and FIG. 7D (systemic tumor model). In the solid tumor model, the area of tumor was determined by measurement of the longest width and length of the tumor with calipers. After complete ablation of the left tumor by cryablation, only contralateral untreated tumor mass was measured. The tumor growth curves of the contralateral alone and mice treated with combination of cryoblation and intratumoral allogeneic Th1 (cryo+Th1). 40% of mice treated with the combination therapy survived without evidence of tumor. The contralateral tumor area is displayed to separately show the response of the 40% mice that survived and the 60% that eventually succumbed to disease. The growth of the contralateral tumors were significantly suppressed (p<0.01) in the 60% of mice that eventually succumbed to disease. In the systemic tumor model (FIG. 7D), mice treated with intratumoral allogeneic Th1 cells alone survived a mean of 28 days, which was significantly longer than control mice which survived a mean of 19 days (logrank: p<010001; hazard ratio=4.291). 40% of mice treated with cryo+Th1 survived >90 days.

Although the present invention has been described with reference to preferred embodiments, workers skilled in the art will recognize that changes may be made in form and detail without departing from the spirit and scope of the invention.

What is claimed is:

1. A method for treating an individual susceptible to one or more diseases comprising:
    developing an anti-alloantigen immunity in an individual by administering a priming composition comprising allogeneic activated Th1 memory cells to the individual, wherein an individual's immune system increases the titer of the circulating anti-alloantigen specific Th1 cells, the priming composition administered prophylactically, prior to onset of the one or more diseases in the individual, wherein the one or more diseases is caused by a pathogen, the allogeneic Th1 memory cells activated by the cross-linking of CD3 and CD28 surface molecules at the time of formulation and administration, the priming composition comprising allogeneic Th1 memory cells, and cross-linking agents for cross-linking the CD3 and CD28 surface moieties on the Th1 memory cells, wherein the anti-alloantigen immunity is developed in the individual prior to administration of one or more disease-related antigens; and
    administering an activating composition comprising allogeneic activated Th1 memory cells, and the one or more disease-related antigens to the primed individual, wherein the activating composition and the one or more disease-related antigens are administered at or after the onset of the one or more diseases in the individual, wherein the one or more diseases is suppressed by the increase in the titer of the circulating Th1 cells in the individual.

2. The method of claim 1 further comprising administering one or more booster compositions comprising allogeneic activated Th1 memory cells to the individual.

3. The method of claim 2 wherein the booster composition further comprises one or more disease-related antigens, wherein the booster composition comprising the one or more disease-related antigens is administered at least about 3-7 days after the previous administration of the allogeneic cells.

4. The method of claim 2 wherein the one or more booster compositions is administered at least about 3-7 days after the previous administration of allogeneic cells.

5. The method of claim 2 wherein the booster composition is from the same source as the priming composition.

6. The method of claim 1 wherein the individual is administered the activating composition at a recurrence of the one or more diseases.

7. The method of claim 1 wherein the one or more diseases affects the Th1 balance in the individual.

8. The method of claim 1 wherein the individual's immune system harbors a Th1 footprint after administration of the priming composition.

\* \* \* \* \*